United States Patent [19]
Dragan

[11] Patent Number: 5,476,381
[45] Date of Patent: Dec. 19, 1995

[54] INTERPROXIMAL DENTAL DISK

[75] Inventor: William B. Dragan, Easton, Conn.

[73] Assignee: Centrix, Inc., Shelton, Conn.

[21] Appl. No.: 299,050

[22] Filed: Aug. 31, 1994

[51] Int. Cl.$^6$ ...................................................... A61C 3/06
[52] U.S. Cl. ........................... 433/142; 433/166; 30/169; 30/314; 451/539; 451/557
[58] Field of Search .................................. 433/125, 141, 433/142, 144, 166; 132/75.6, 76.4; 451/539, 540, 552, 557; 30/169, 314

[56] References Cited

U.S. PATENT DOCUMENTS

| | | | |
|---|---|---|---|
| 522,211 | 7/1894 | How | 433/144 |
| 527,859 | 10/1894 | Ingram | 30/169 |
| 781,587 | 1/1905 | Blake | 433/166 |
| 842,074 | 1/1907 | Bryan | 30/169 |
| 4,483,676 | 11/1984 | Thierman | 433/142 |
| 4,738,621 | 4/1988 | Lowder | 433/142 |

*Primary Examiner*—Stephen Funk
*Attorney, Agent, or Firm*—Fattibene and Fattibene; Arthur T. Fattibene; Paul A. Fattibene

[57] ABSTRACT

A dental interproximal disk formed of rigid sheet material as a unitary or integrally formed handle portion and blade portion with an arcuate cutting edge. The handle portion includes a plurality of corrugated flutes terminating in a laterally offset flange. The side surfaces of the blade portions may be either smooth or roughened on one or both surfaces thereof. An aperture is formed adjacent one end of the handle portion for attachment of a string or cord to effect retrieving if necessary as a matter of safety.

12 Claims, 1 Drawing Sheet

INTERPROXIMAL DENTAL DISK

FIELD OF THE INVENTION

This invention relates to a new and improved interproximal dental disk.

BACKGROUND OF THE INVENTION

Heretofore, interproximal disks have been used in dentistry as evidenced by U.S. Pat. No. 4,483,676 granted Nov. 20, 1984. Such known interproximal disk consisted of a circular metallic disk which was provided with a plastic molded handle to provide the means whereby the dentist could grip the interproximal disk. The plastic handle was attached to the disk by injection molding. Such molding of the plastic handle to the disk required the disk to be formed with a pair of apertures through which the plastic of the handle would be allowed to flow during forming to form molded plugs for securely attaching the plastic handle to the metallic disk.

An object of the present invention is to provide an interproximal disk having a blade portion and a handle portion integrally formed of a rigid sheet of metallic material which is devoid of any plastic component.

Another object is to provide an all metallic interproximal disk which is totally sterilizable by all known forms of sterilization.

Another object is to provide an interproximal disk which can be readily and inexpensively formed by stamping from a sheet of metallic material which is simple in construction and positive in operation.

SUMMARY OF THE INVENTION

The foregoing objects and other features and advantages of the invention are attained by a unitary interproximal disk formed from a sheet of metallic material by stamping. The interproximal disk includes a blade portion having an arcuate working or cutting edge with a unitary or integrally formed handle portion. The unitary or integrally formed blade and handle portions are blanked out of a thin sheet of metallic material having a thickness preferably ranging between 0.008 and 0.003 inches. The handle portion is provided with a plurality of corrugated flutes to impart rigidity to the relatively thin interproximal disk structure which terminates into a laterally offset flange disposed normal to the blade portion. The handle portion projects or extends beyond the blade portion. The extended handle portion is provided with an aperture to which a retrieving cord may be attached. In accordance with this invention, one or both side surfaces of the blade portion may be made smooth and/or may be roughened to provide an abrasive surface for the purpose of smoothing the contact areas between adjacent teeth when the interproximal disk is used.

IN THE DRAWINGS

DETAILED DESCRIPTION OF THE INVENTION

In the practice of dentistry, it is frequently necessary to maintain the contact area between adjacent teeth free to allow the insertion of dental floss or rubber dams. Frequently, during a tooth restoration or other dental procedure, the space between the adjacent teeth may tend to close due to any excess bonding agent, cement, amalgam or other dental material becoming entrapped therein. Therefore, it is imperative that some means be provided whereby the dentist may remove such material from between adjacent teeth and/or to provide a slight expansion of the contact area as may be required.

Figure 1:
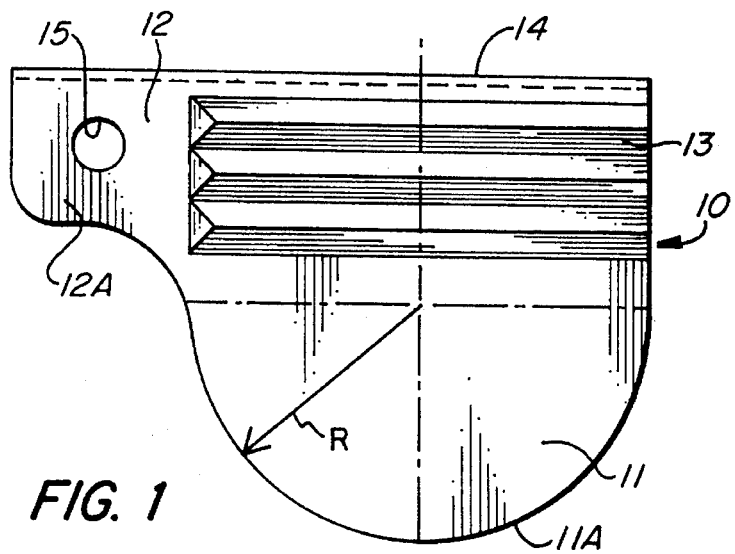
FIG. 1 is a side elevational view of an interproximal disk embodying the invention.
Figure 3:
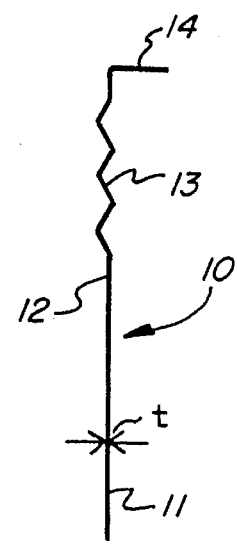
FIG. 3 is an end view of FIG. 1.
Figure 2:
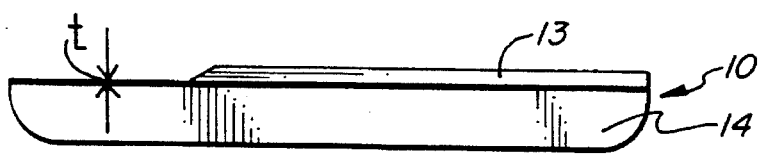
FIG. 2 is a top plan view of FIG. 1.

According to this invention, a new and improved interproximal disk is provided by which the dentist can maintain the contact area between adjacent teeth. Referring to FIGS. 1 to 3, the illustrated interproximal disk 10 comprises a blade portion 11 and an integrally connected handle portion 12. The integral interproximal disk 10 is preferably formed from a relatively thin sheet of metallic material, e.g. stainless steel, having a thickness "t" ranging between 0.008 to 0.003 inches by stamping, wherein the optimal thickness for most purposes is approximately 0.005 inches. As shown, the blade portion 11 is provided with an arcuate working or cutting edge 11A. The radius R of the cutting edge is approximately 0.445 inch. The cutting edge 11A is not sharpened. The arrangement is such that the thickness of the blade portion 11 and handle portion 12 is the thickness of the material of which it is formed, e.g. ranging between 0.008 and 0.003 inches. However, the blade portion 11 is sufficiently thin so as to fit within the contact space between adjacent teeth to either smooth the contact area and/or remove the excess dental material tending to collect within the contact area during a dental procedure.

To provide rigidity of the interproximal disk 10, the handle portion 12 is provided with a series of corrugated flutes 13 wherein the upper end of the handle portion terminates into a laterally offset flange 14 disposed substantially normal relative to the blade portion. Thus, the offset flange 14 and the corrugated flutes 13 provide substantial rigidity to the handle portion while the thin blade portion can maintain the limited flexibility inherent by the thinness of the blade portion 11. The construction of the interproximal disk thus described allows the blade portion 11 to be capable of insertion through the space or contact area between adjacent teeth to effect the clearing out of any excess bonding material, cement or any other dental material accumulated therein as the result of any dental procedure.

Normally, the interproximal disk is held between the thumb and middle finger of the operator with the index finger pressing on the lateral offset flange 14 to provide the necessary downward pressure to cut through the dental material to be removed from the contact area. In the illustrated embodiment of FIGS. 1 to 3, the opposed side surfaces of the cutting blade 11 are made smooth. Such smooth surface blade portion allows for effecting the cutting away or removal of the dental material entrapped within the contact area without effecting any polishing or smoothing effect upon the adjacent teeth.

Figure 4:
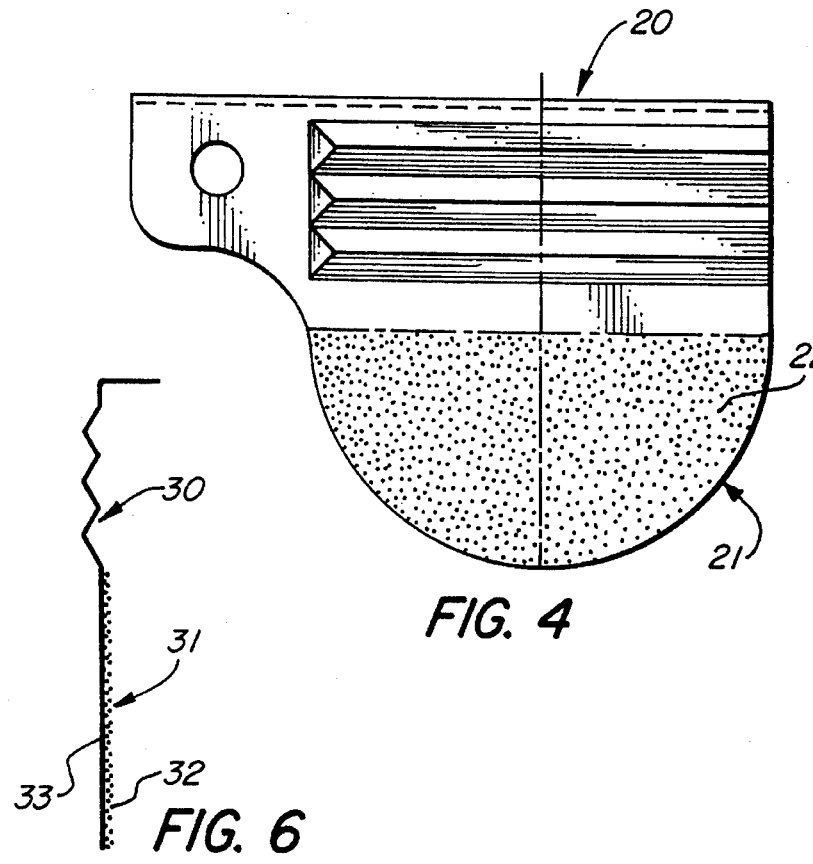
FIG. 4 is a side elevational view of a modified form of the invention.
Figure 5:
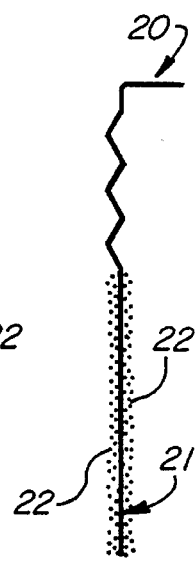
FIG. 5 is an end view of the embodiment of FIG. 4.

However, in the event that a polishing or smoothing effect is desired upon the adjacent teeth, the blade portion of the interproximal disk may be provided with an abrasive surface. FIGS. 4 and 5 illustrate a modified embodiment 20 of the invention, wherein the opposed surfaces of the blade portion 21 are roughened as indicated at 22 to provide an abrasive surface. In this form of the invention, it will be apparent that the interproximal disk can effect the cutting and/or removal of the bonding agent, cement or other material from within the contact area and at the same time, effect the smoothing or polishing of the adjacent teeth, as may be required. In all other respects, the construction of the interproximal disk 20 of FIGS. 4 and 5 is the same as that described with respect to FIGS. 1 to 3.

Figure 6:
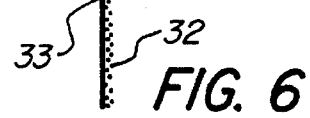
FIG. 6 is an end view of another embodiment of the invention.

FIG. 6 illustrates a further embodiment of the invention. In this form of the invention, the interproximal disk 30 is provided with a blade portion 31 which is roughened on one surface as indicated at 32 and smooth on the other side as indicated at 33. In this form, it will be apparent that the contact surface on one side of the blade portion 31 can be smoothed, while the contact surface on the other side of the blade portion 31 is not subjected to a smoothing action. The embodiment of FIG. 6 is utilized when only one contact surface requires smoothing and not the other. When the contact surface of adjacent teeth both require smoothing, the interproximal disk of FIG. 4 is recommended. In all other respects, the construction of the embodiment of FIG. 6 is similar to that of FIGS. 1 to 3, herein described.

Referring again to FIGS. 1 to 3, it will be noted that the handle portion 12 projects laterally beyond one edge of the blade portion 11. The laterally extended portion 12A of the handle portion 12 is provided with an aperture or opening 15 to which a cord or floss (not shown) may be attached. The cord or floss attached to the interproximal disk functions as a retrieval line for the purpose of retrieving the interproximal disk in the event that it should be accidentally dropped into the patient's mouth. The embodiments of FIGS. 4 and 6 are provided with a similar handle structure.

In operation, the dentist or operator can firmly grip the interproximal disk between his or her thumb and middle finger with the index finger pressing against the lateral flange 14. With such grip, the dentist forces the working or cutting edge of the blade portion 11 into the contact area between adjacent teeth and with one or more parallel motions, smooth out the roughness of the contact area; providing the blade portion is formed with a roughened area as herein described with respect to the embodiments of FIGS. 4 and/or 6. By further penetration of the interproximal disk into the contact area, the excess bonding material, cement or other dental material can be cleared out of the contact area. The thinness or the blade portion 11 is sufficient to push out or cut through any excess material trapped within the contact area.

The roughened area of the blade portion as described with respect to FIGS. 4 and 6 is accomplished by sandblasting the surface of the blade. The surfaces of the blade portion can also be toughened by utilizing suitable abrasive particles which can be adhered to the surface of the blade by any suitable adhesive.

From the foregoing, it will be apparent that the handle portion, although blanked from the same thin material as the blade portion, is nevertheless rendered sufficiently more rigid by the corrugated flutes 13 and lateral flange 14 so as to resist any flexing, twisting, or torquing of the handle portion during use of the interproximal disk.

The described construction renders the interproximal disk to be formed as a unitary all metal member, e.g. stainless steel, thereby rendering the device completely sterilizable, e.g. by steam autoclaving, dry heat, chemical autoclaving, or any other means of sterilizing. This is rendered possible because the described interproximal disk does not incorporate any plastic component.

While the present invention has been described with respect to several embodiments, it will be apparent that various modifications may be made without departing from the spirit and scope of this invention.

What is claimed is:

1. An interproximal disk for use in dentistry comprising:
    a blank of rigid sheet material having an upper handle portion and an integrally formed blade portion having an arcuate cutting edge,
    said handle portion including a plurality of corrugated flutes formed a plane thereof and terminating in a lateral flange,
    and an aperture formed in said handle portion adjacent one end thereon.

2. An interproximal disk as defined in claim 1 and including said blade portion having a toughened side surface.

3. An interproximal disk as defined in claim 1 wherein said blade portion includes opposed roughened surfaces.

4. An interproximal disk as defined in claim 1 wherein said blade portion includes opposed smooth side surfaces.

5. An interproximal disk as defined in claim 1 wherein said blade portion is substantially semi-circular.

6. An interproximal disk as defined in claim 1 wherein said handle portion includes a projected end extending laterally to one side of said blade portion.

7. An interproximal disk as defined in claim 6 wherein said aperture is disposed in the projected end of said handle portion.

8. An interproximal disk as defined in claim 1 wherein said blade portion has a thickness ranging between 0.008 to 0.003 inches.

9. An interproximal disk as defined in claim 1 wherein said handle portion and said blade portion are unitarily formed of a sheet metal having a cross section of uniform thickness.

10. An interproximal disk as defined in claim 9 wherein said metal is stainless steel.

11. An interproximal disk as defined in claim 1 wherein said blade portion is smooth on one surface and roughened on the other surface thereof.

12. An interproximal disk for use in dentistry comprising:
    a handle portion and a blade portion unitarily formed from a block of rigid sheet material of stainless steel,
    said handle portion and unitarily formed blade portion having a cross-sectional thickness ranging between 0.008 to 0.003 inches,
    said blade portion having a semi-circular cutting edge,
    and said handle portion including a plurality of corrugated flutes extending longitudinally of said handle portion, and an upper edge terminating in a lateral offset flange disposed substantially normal to said blade portion,
    said handle portion having a projecting end portion extending beyond said blade portion,
    an aperture formed in said projected end portion of said handle portion,
    said blade portion having a roughened surface on at least one side thereof, and
    said roughened surface being formed by sand blasting.

* * * * *